US007029849B2

(12) United States Patent
Salonen

(10) Patent No.: US 7,029,849 B2
(45) Date of Patent: Apr. 18, 2006

(54) METHOD FOR DETECTING A RISK OF HYPERTENSION AND USES THEREOF

(75) Inventor: Jukka T. Salonen, Jännevirta (FI)

(73) Assignee: Oy Jurilab Ltd., Kuopio (FI)

( * ) Notice: Subject to any disclaimer, the term of this patent is extended or adjusted under 35 U.S.C. 154(b) by 399 days.

(21) Appl. No.: 10/077,870

(22) Filed: Feb. 20, 2002

(65) Prior Publication Data

US 2003/0003470 A1    Jan. 2, 2003

(30) Foreign Application Priority Data

Feb. 20, 2001   (FI)   ................................. 20010323

(51) Int. Cl.
*C12Q 1/68*   (2006.01)
*C12P 19/34*  (2006.01)
*C07H 21/02*  (2006.01)
*C07H 21/04*  (2006.01)

(52) U.S. Cl. .................. 435/6; 435/91.2; 536/23.5; 536/24.31; 536/24.33

(58) Field of Classification Search ............. 435/6, 435/91.2; 536/23.1, 24.3
See application file for complete search history.

(56) References Cited

U.S. PATENT DOCUMENTS 5,595,880 A    1/1997   Weinshank et al.

FOREIGN PATENT DOCUMENTS

WO    WO 99/52942    * 10/1999
WO    WO 01/29082       4/2001

OTHER PUBLICATIONS

Small et al.(Journal of Biological Chemistry, vol. 267, No. 7, Feb., 16 2001).*
Heinonen et al, J. Clin. Endocrinol. vol. 84, No. 7 1999.*
Baldwin et al. Am J. Hypertens. 12:853-857,1999 (Abstract).*
Munroe, P.B. et al. Curr.Opin. Genet. Dev. 10::325-329: 2000.*
Von Wowern et al.(Hypertension. 2004; 43: 592).*
Hacker et al.(Gut, 1997, vol. 40, pp. 623-627).*
Pennisi, Science, 281 (5384):1787-1789.*
Baldwin et al.(American Journal of Hypertension, 1999; 12:853-857).*
Heinonen et al.(The Journal of Clinical Endocrinology and Metabolism vol. 84, No. 7 1999, 2429-2433).*
Baldwin et al., "Identification of a Polymorphic Glutamic . . . ", *American Journal of Hypertension*, vol. 12, 1999, pp. 853-857.
Small et al., "Polymorphic Deletion of Three Intracellular . . . ", *The Journal of Biological Chemistry*, vol. 276, No. 7, 2001, pp. 4917-4922.
Snapir et al., "An Insertion/Deletion Polymorphism . . . ", *Journal of the American College of Cardiology*, vol. 37, No. 6, 2001, pp. 1516-1522.
Jewell-Motz et al., "An Acidic Motif within the Third Intracellular . . . ", *Biochemistry*, vol. 34, 1995, pp. 11946-11953.
Heinonen, et al., "Identification of a Three-Amino Acid Deletion . . . ", *The Journal of Clinical Endocrinology and Metabolism*, vol. 84, No. 7, 1999, pp. 2429-2433.

* cited by examiner

*Primary Examiner*—W. Gary Jones
*Assistant Examiner*—Sally A. Sakelaris
(74) *Attorney, Agent, or Firm*—Birch, Stewart, Kolasch & Birch, LLP

(57) ABSTRACT

This invention relates to a method for detecting a risk of hypertension and for targeting antihypertensive treatment in a subject, the method comprising isolating genomic DNA from said subject, determining the DNA sequence comprising a nucleotide sequence encoding a variant $\alpha_{2B}$-adrenoceptor protein.

21 Claims, No Drawings

SEQUENCE LISTING

<160> NUMBER OF SEQ ID NOS: 10

<210> SEQ ID NO 1
<211> LENGTH: 1344
<212> TYPE: DNA
<213> ORGANISM: Homo sapiens
<220> FEATURE:
<221> NAME/KEY: CDS
<222> LOCATION: (1)..(1341)
<223> OTHER INFORMATION: Coding sequence for variant human alpha-2B-
      adrenoceptor protein

<400> SEQUENCE: 1

| | | | | | | | | | | | | | | | | |
|---|---|---|---|---|---|---|---|---|---|---|---|---|---|---|---|---|
| atg | gac | cac | cag | gac | ccc | tac | tcc | gtg | cag | gcc | aca | gcg | gcc | ata | gcg | 48 |
| Met | Asp | His | Gln | Asp | Pro | Tyr | Ser | Val | Gln | Ala | Thr | Ala | Ala | Ile | Ala | |
| 1 | | | | 5 | | | | | 10 | | | | | 15 | | |

| gcg | gcc | atc | acc | ttc | ctc | att | ctc | ttt | acc | atc | ttc | ggc | aac | gct | ctg | 96 |
|---|---|---|---|---|---|---|---|---|---|---|---|---|---|---|---|---|
| Ala | Ala | Ile | Thr | Phe | Leu | Ile | Leu | Phe | Thr | Ile | Phe | Gly | Asn | Ala | Leu |
| | | | 20 | | | | | 25 | | | | | 30 | | |

| gtc | atc | ctg | gct | gtg | ttg | acc | agc | cgc | tcg | ctg | cgc | gcc | cct | cag | aac | 144 |
|---|---|---|---|---|---|---|---|---|---|---|---|---|---|---|---|---|
| Val | Ile | Leu | Ala | Val | Leu | Thr | Ser | Arg | Ser | Leu | Arg | Ala | Pro | Gln | Asn |
| | 35 | | | | | 40 | | | | | 45 | | | | |

| ctg | ttc | ctg | gtg | tcg | ctg | gcc | gcc | gcc | gac | atc | ctg | gtg | gcc | acg | ctc | 192 |
|---|---|---|---|---|---|---|---|---|---|---|---|---|---|---|---|---|
| Leu | Phe | Leu | Val | Ser | Leu | Ala | Ala | Ala | Asp | Ile | Leu | Val | Ala | Thr | Leu |
| 50 | | | | | 55 | | | | | 60 | | | | | |

| atc | atc | cct | ttc | tcg | ctg | gcc | aac | gag | ctg | ctg | ggc | tac | tgg | tac | ttc | 240 |
|---|---|---|---|---|---|---|---|---|---|---|---|---|---|---|---|---|
| Ile | Ile | Pro | Phe | Ser | Leu | Ala | Asn | Glu | Leu | Leu | Gly | Tyr | Trp | Tyr | Phe |
| 65 | | | | | 70 | | | | | 75 | | | | | 80 |

| cgg | cgc | acg | tgg | tgc | gag | gtg | tac | ctg | gcg | ctc | gac | gtg | ctc | ttc | tgc | 288 |
|---|---|---|---|---|---|---|---|---|---|---|---|---|---|---|---|---|
| Arg | Arg | Thr | Trp | Cys | Glu | Val | Tyr | Leu | Ala | Leu | Asp | Val | Leu | Phe | Cys |
| | | | | 85 | | | | | 90 | | | | | 95 | |

| acc | tcg | tcc | atc | gtg | cac | ctg | tgc | gcc | atc | agc | ctg | gac | cgc | tac | tgg | 336 |
|---|---|---|---|---|---|---|---|---|---|---|---|---|---|---|---|---|
| Thr | Ser | Ser | Ile | Val | His | Leu | Cys | Ala | Ile | Ser | Leu | Asp | Arg | Tyr | Trp |
| | | | 100 | | | | | 105 | | | | | 110 | | |

| gcc | gtg | agc | cgc | gcg | ctg | gag | tac | aac | tcc | aag | cgc | acc | ccg | cgc | cgc | 384 |
|---|---|---|---|---|---|---|---|---|---|---|---|---|---|---|---|---|
| Ala | Val | Ser | Arg | Ala | Leu | Glu | Tyr | Asn | Ser | Lys | Arg | Thr | Pro | Arg | Arg |
| | 115 | | | | | 120 | | | | | 125 | | | | |

| atc | aag | tgc | atc | atc | ctc | act | gtg | tgg | ctc | atc | gcc | gcc | gtc | atc | tcg | 432 |
|---|---|---|---|---|---|---|---|---|---|---|---|---|---|---|---|---|
| Ile | Lys | Cys | Ile | Ile | Leu | Thr | Val | Trp | Leu | Ile | Ala | Ala | Val | Ile | Ser |
| 130 | | | | | 135 | | | | | 140 | | | | | |

| ctg | ccg | ccc | ctc | atc | tac | aag | ggc | gac | cag | ggc | ccc | cag | ccg | cgc | ggg | 480 |
|---|---|---|---|---|---|---|---|---|---|---|---|---|---|---|---|---|
| Leu | Pro | Pro | Leu | Ile | Tyr | Lys | Gly | Asp | Gln | Gly | Pro | Gln | Pro | Arg | Gly |
| 145 | | | | | 150 | | | | | 155 | | | | | 160 |

| cgc | ccc | cag | tgc | aag | ctc | aac | cag | gag | gcc | tgg | tac | atc | ctg | gcc | tcc | 528 |
|---|---|---|---|---|---|---|---|---|---|---|---|---|---|---|---|---|
| Arg | Pro | Gln | Cys | Lys | Leu | Asn | Gln | Glu | Ala | Trp | Tyr | Ile | Leu | Ala | Ser |
| | | | | 165 | | | | | 170 | | | | | 175 | |

| agc | atc | gga | tct | ttc | ttt | gct | cct | tgc | ctc | atc | atg | atc | ctt | gtc | tac | 576 |
|---|---|---|---|---|---|---|---|---|---|---|---|---|---|---|---|---|
| Ser | Ile | Gly | Ser | Phe | Phe | Ala | Pro | Cys | Leu | Ile | Met | Ile | Leu | Val | Tyr |
| | | | 180 | | | | | 185 | | | | | 190 | | |

| ctg | cgc | atc | tac | ctg | atc | gcc | aaa | cgc | agc | aac | cgc | aga | ggt | ccc | agg | 624 |
|---|---|---|---|---|---|---|---|---|---|---|---|---|---|---|---|---|
| Leu | Arg | Ile | Tyr | Leu | Ile | Ala | Lys | Arg | Ser | Asn | Arg | Arg | Gly | Pro | Arg |
| | 195 | | | | | 200 | | | | | 205 | | | | |

| gcc | aag | ggg | ggg | cct | ggg | cag | ggt | gag | tcc | aag | cag | ccc | cga | ccc | gac | 672 |
|---|---|---|---|---|---|---|---|---|---|---|---|---|---|---|---|---|
| Ala | Lys | Gly | Gly | Pro | Gly | Gln | Gly | Glu | Ser | Lys | Gln | Pro | Arg | Pro | Asp |
| 210 | | | | | 215 | | | | | 220 | | | | | |

| cat | ggt | ggg | gct | ttg | gcc | tca | gcc | aaa | ctg | cca | gcc | ctg | gcc | tct | gtg | 720 |
|---|---|---|---|---|---|---|---|---|---|---|---|---|---|---|---|---|
| His | Gly | Gly | Ala | Leu | Ala | Ser | Ala | Lys | Leu | Pro | Ala | Leu | Ala | Ser | Val |
| 225 | | | | | 230 | | | | | 235 | | | | | 240 |

| gct | tct | gcc | aga | gag | gtc | aac | gga | cac | tcg | aag | tcc | act | ggg | gag | aag | 768 |
|---|---|---|---|---|---|---|---|---|---|---|---|---|---|---|---|---|
| Ala | Ser | Ala | Arg | Glu | Val | Asn | Gly | His | Ser | Lys | Ser | Thr | Gly | Glu | Lys |

-continued

```
                    245                 250                 255
gag gag ggg gag acc cct gaa gat act ggg acc cgg gcc ttg cca ccc       816
Glu Glu Gly Glu Thr Pro Glu Asp Thr Gly Thr Arg Ala Leu Pro Pro
            260                 265                 270 agt tgg gct gcc ctt ccc aac tca ggc cag ggc cag aag gag ggt gtt       864
Ser Trp Ala Ala Leu Pro Asn Ser Gly Gln Gly Gln Lys Glu Gly Val
        275                 280                 285 tgt ggg gca tct cca gag gat gaa gct gaa gag gaa gag gag gag gag       912
Cys Gly Ala Ser Pro Glu Asp Glu Ala Glu Glu Glu Glu Glu Glu Glu
    290                 295                 300 gag gag tgt gaa ccc cag gca gtg cca gtg tct ccg gcc tca gct tgc       960
Glu Glu Cys Glu Pro Gln Ala Val Pro Val Ser Pro Ala Ser Ala Cys
305                 310                 315                 320 agc ccc ccg ctg cag cag cca cag ggc tcc cgg gtg ctg gcc acc cta      1008
Ser Pro Pro Leu Gln Gln Pro Gln Gly Ser Arg Val Leu Ala Thr Leu
                325                 330                 335 cgt ggc cag gtg ctc ctg ggc agg ggc gtg ggt gct ata ggt ggg cag      1056
Arg Gly Gln Val Leu Leu Gly Arg Gly Val Gly Ala Ile Gly Gly Gln
            340                 345                 350 tgg tgg cgt cga cgg gcg cag ctg acc cgg gag aag cgc ttc acc ttc      1104
Trp Trp Arg Arg Arg Ala Gln Leu Thr Arg Glu Lys Arg Phe Thr Phe
        355                 360                 365 gtg ctg gct gtg gtc att ggc gtt ttt gtg ctc tgc tgg ttc ccc ttc      1152
Val Leu Ala Val Val Ile Gly Val Phe Val Leu Cys Trp Phe Pro Phe
    370                 375                 380 ttc ttc agc tac agc ctg ggc gcc atc tgc ccg aag cac tgc aag gtg      1200
Phe Phe Ser Tyr Ser Leu Gly Ala Ile Cys Pro Lys His Cys Lys Val
385                 390                 395                 400 ccc cat ggc ctc ttc cag ttc ttc ttc tgg atc ggc tac tgc aac agc      1248
Pro His Gly Leu Phe Gln Phe Phe Phe Trp Ile Gly Tyr Cys Asn Ser
                405                 410                 415 tca ctg aac cct gtt atc tac acc atc ttc aac cag gac ttc cgc cgt      1296
Ser Leu Asn Pro Val Ile Tyr Thr Ile Phe Asn Gln Asp Phe Arg Arg
            420                 425                 430 gcc ttc cgg agg atc ctg tgc cgc ccg tgg acc cag acg gcc tgg tga      1344
Ala Phe Arg Arg Ile Leu Cys Arg Pro Trp Thr Gln Thr Ala Trp
        435                 440                 445
```

<210> SEQ ID NO 2
<211> LENGTH: 447
<212> TYPE: PRT
<213> ORGANISM: Homo sapiens

<400> SEQUENCE: 2

```
Met Asp His Gln Asp Pro Tyr Ser Val Gln Ala Thr Ala Ala Ile Ala
  1               5                  10                  15

Ala Ala Ile Thr Phe Leu Ile Leu Phe Thr Ile Phe Gly Asn Ala Leu
             20                  25                  30

Val Ile Leu Ala Val Leu Thr Ser Arg Ser Leu Arg Ala Pro Gln Asn
         35                  40                  45

Leu Phe Leu Val Ser Leu Ala Ala Ala Asp Ile Leu Val Ala Thr Leu
     50                  55                  60

Ile Ile Pro Phe Ser Leu Ala Asn Glu Leu Leu Gly Tyr Trp Tyr Phe
 65                  70                  75                  80

Arg Arg Thr Trp Cys Glu Val Tyr Leu Ala Leu Asp Val Leu Phe Cys
                 85                  90                  95

Thr Ser Ser Ile Val His Leu Cys Ala Ile Ser Leu Asp Arg Tyr Trp
            100                 105                 110
```

```
Ala Val Ser Arg Ala Leu Glu Tyr Asn Ser Lys Arg Thr Pro Arg Arg
            115                 120                 125

Ile Lys Cys Ile Ile Leu Thr Val Trp Leu Ile Ala Ala Val Ile Ser
130                 135                 140

Leu Pro Pro Leu Ile Tyr Lys Gly Asp Gln Gly Pro Gln Pro Arg Gly
145                 150                 155                 160

Arg Pro Gln Cys Lys Leu Asn Gln Glu Ala Trp Tyr Ile Leu Ala Ser
            165                 170                 175

Ser Ile Gly Ser Phe Phe Ala Pro Cys Leu Ile Met Ile Leu Val Tyr
            180                 185                 190

Leu Arg Ile Tyr Leu Ile Ala Lys Arg Ser Asn Arg Arg Gly Pro Arg
            195                 200                 205

Ala Lys Gly Gly Pro Gly Gln Gly Glu Ser Lys Gln Pro Arg Pro Asp
210                 215                 220

His Gly Gly Ala Leu Ala Ser Ala Lys Leu Pro Ala Leu Ala Ser Val
225                 230                 235                 240

Ala Ser Ala Arg Glu Val Asn Gly His Ser Lys Ser Thr Gly Glu Lys
            245                 250                 255

Glu Glu Gly Glu Thr Pro Glu Asp Thr Gly Thr Arg Ala Leu Pro Pro
            260                 265                 270

Ser Trp Ala Ala Leu Pro Asn Ser Gly Gln Gly Gln Lys Glu Gly Val
            275                 280                 285

Cys Gly Ala Ser Pro Glu Asp Glu Ala Glu Glu Glu Glu Glu Glu Glu
            290                 295                 300

Glu Glu Cys Glu Pro Gln Ala Val Pro Val Ser Pro Ala Ser Ala Cys
305                 310                 315                 320

Ser Pro Pro Leu Gln Gln Pro Gln Gly Ser Arg Val Leu Ala Thr Leu
            325                 330                 335

Arg Gly Gln Val Leu Leu Gly Arg Gly Val Gly Ala Ile Gly Gly Gln
            340                 345                 350

Trp Trp Arg Arg Arg Ala Gln Leu Thr Arg Glu Lys Arg Phe Thr Phe
            355                 360                 365

Val Leu Ala Val Val Ile Gly Val Phe Val Leu Cys Trp Phe Pro Phe
370                 375                 380

Phe Phe Ser Tyr Ser Leu Gly Ala Ile Cys Pro Lys His Cys Lys Val
385                 390                 395                 400

Pro His Gly Leu Phe Gln Phe Phe Trp Ile Gly Tyr Cys Asn Ser
            405                 410                 415

Ser Leu Asn Pro Val Ile Tyr Thr Ile Phe Asn Gln Asp Phe Arg Arg
            420                 425                 430

Ala Phe Arg Arg Ile Leu Cys Arg Pro Trp Thr Gln Thr Ala Trp
            435                 440                 445
```

<210> SEQ ID NO 3
<211> LENGTH: 1353
<212> TYPE: DNA
<213> ORGANISM: Homo sapiens
<220> FEATURE:
<221> NAME/KEY: CDS
<222> LOCATION: (1)..(1350)
<223> OTHER INFORMATION: Coding sequence for human alpha-2B-adrenoceptor protein

<400> SEQUENCE: 3

```
atg gac cac cag gac ccc tac tcc gtg cag gcc aca gcg gcc ata gcg      48
Met Asp His Gln Asp Pro Tyr Ser Val Gln Ala Thr Ala Ala Ile Ala
 1               5                  10                  15
```

-continued

| | |
|---|---|
| gcg gcc atc acc ttc ctc att ctc ttt acc atc ttc ggc aac gct ctg<br>Ala Ala Ile Thr Phe Leu Ile Leu Phe Thr Ile Phe Gly Asn Ala Leu<br>                 20                        25                       30 | 96 |
| gtc atc ctg gct gtg ttg acc agc cgc tcg ctg cgc gcc cct cag aac<br>Val Ile Leu Ala Val Leu Thr Ser Arg Ser Leu Arg Ala Pro Gln Asn<br>         35                     40                   45 | 144 |
| ctg ttc ctg gtg tcg ctg gcc gcc gcc gac atc ctg gtg gcc acg ctc<br>Leu Phe Leu Val Ser Leu Ala Ala Ala Asp Ile Leu Val Ala Thr Leu<br>50                     55                     60 | 192 |
| atc atc cct ttc tcg ctg gcc aac gag ctg ctg ggc tac tgg tac ttc<br>Ile Ile Pro Phe Ser Leu Ala Asn Glu Leu Leu Gly Tyr Trp Tyr Phe<br>65                     70                     75                     80 | 240 |
| cgg cgc acg tgg tgc gag gtg tac ctg gcg ctc gac gtg ctc ttc tgc<br>Arg Arg Thr Trp Cys Glu Val Tyr Leu Ala Leu Asp Val Leu Phe Cys<br>                   85                       90                       95 | 288 |
| acc tcg tcc atc gtg cac ctg tgc gcc atc agc ctg gac cgc tac tgg<br>Thr Ser Ser Ile Val His Leu Cys Ala Ile Ser Leu Asp Arg Tyr Trp<br>                 100                  105               110 | 336 |
| gcc gtg agc cgc gcg ctg gag tac aac tcc aag cgc acc ccg cgc cgc<br>Ala Val Ser Arg Ala Leu Glu Tyr Asn Ser Lys Arg Thr Pro Arg Arg<br>         115                    120                125 | 384 |
| atc aag tgc atc atc ctc act gtg tgg ctc atc gcc gcc gtc atc tcg<br>Ile Lys Cys Ile Ile Leu Thr Val Trp Leu Ile Ala Ala Val Ile Ser<br>130                   135                  140 | 432 |
| ctg ccg ccc ctc atc tac aag ggc gac cag ggc ccc cag ccg cgc ggg<br>Leu Pro Pro Leu Ile Tyr Lys Gly Asp Gln Gly Pro Gln Pro Arg Gly<br>145                   150                  155                160 | 480 |
| cgc ccc cag tgc aag ctc aac cag gag gcc tgg tac atc ctg gcc tcc<br>Arg Pro Gln Cys Lys Leu Asn Gln Glu Ala Trp Tyr Ile Leu Ala Ser<br>                 165                  170               175 | 528 |
| agc atc gga tct ttc ttt gct cct tgc ctc atc atg atc ctt gtc tac<br>Ser Ile Gly Ser Phe Phe Ala Pro Cys Leu Ile Met Ile Leu Val Tyr<br>                 180                  185               190 | 576 |
| ctg cgc atc tac ctg atc gcc aaa cgc agc aac cgc aga ggt ccc agg<br>Leu Arg Ile Tyr Leu Ile Ala Lys Arg Ser Asn Arg Arg Gly Pro Arg<br>         195                    200                205 | 624 |
| gcc aag ggg ggg cct ggg cag ggt gag tcc aag cag ccc cga ccc gac<br>Ala Lys Gly Gly Pro Gly Gln Gly Glu Ser Lys Gln Pro Arg Pro Asp<br>210                   215                  220 | 672 |
| cat ggt ggg gct ttg gcc tca gcc aaa ctg cca gcc ctg gcc tct gtg<br>His Gly Gly Ala Leu Ala Ser Ala Lys Leu Pro Ala Leu Ala Ser Val<br>225                   230                  235                240 | 720 |
| gct tct gcc aga gag gtc aac gga cac tcg aag tcc act ggg gag aag<br>Ala Ser Ala Arg Glu Val Asn Gly His Ser Lys Ser Thr Gly Glu Lys<br>                 245                  250               255 | 768 |
| gag gag ggg gag acc cct gaa gat act ggg acc cgg gcc ttg cca ccc<br>Glu Glu Gly Glu Thr Pro Glu Asp Thr Gly Thr Arg Ala Leu Pro Pro<br>                 260                  265               270 | 816 |
| agt tgg gct gcc ctt ccc aac tca ggc cag ggc cag aag gag ggt gtt<br>Ser Trp Ala Ala Leu Pro Asn Ser Gly Gln Gly Gln Lys Glu Gly Val<br>         275                    280                285 | 864 |
| tgt ggg gca tct cca gag gat gaa gct gaa gag gag gaa gag gag gag<br>Cys Gly Ala Ser Pro Glu Asp Glu Ala Glu Glu Glu Glu Glu Glu Glu<br>290                   295                  300 | 912 |
| gag gag gag gaa gag tgt gaa ccc cag gca gtg cca gtg tct ccg gcc<br>Glu Glu Glu Glu Glu Cys Glu Pro Gln Ala Val Pro Val Ser Pro Ala<br>305                   310                  315                320 | 960 |
| tca gct tgc agc ccc ccg ctg cag cag cca cag ggc tcc cgg gtg ctg<br>Ser Ala Cys Ser Pro Pro Leu Gln Gln Pro Gln Gly Ser Arg Val Leu | 1008 |

```
                              325                 330                 335
gcc acc cta cgt ggc cag gtg ctc ctg ggc agg ggc gtg ggt gct ata         1056
Ala Thr Leu Arg Gly Gln Val Leu Leu Gly Arg Gly Val Gly Ala Ile
            340                 345                 350 ggt ggg cag tgg tgg cgt cga cgg gcg cag ctg acc cgg gag aag cgc         1104
Gly Gly Gln Trp Trp Arg Arg Arg Ala Gln Leu Thr Arg Glu Lys Arg
        355                 360                 365 ttc acc ttc gtg ctg gct gtg gtc att ggc gtt ttt gtg ctc tgc tgg         1152
Phe Thr Phe Val Leu Ala Val Val Ile Gly Val Phe Val Leu Cys Trp
    370                 375                 380 ttc ccc ttc ttc ttc agc tac agc ctg ggc gcc atc tgc ccg aag cac         1200
Phe Pro Phe Phe Phe Ser Tyr Ser Leu Gly Ala Ile Cys Pro Lys His
385                 390                 395                 400 tgc aag gtg ccc cat ggc ctc ttc cag ttc ttc ttc tgg atc ggc tac         1248
Cys Lys Val Pro His Gly Leu Phe Gln Phe Phe Phe Trp Ile Gly Tyr
                405                 410                 415 tgc aac agc tca ctg aac cct gtt atc tac acc atc ttc aac cag gac         1296
Cys Asn Ser Ser Leu Asn Pro Val Ile Tyr Thr Ile Phe Asn Gln Asp
            420                 425                 430 ttc cgc cgt gcc ttc cgg agg atc ctg tgc cgc ccg tgg acc cag acg         1344
Phe Arg Arg Ala Phe Arg Arg Ile Leu Cys Arg Pro Trp Thr Gln Thr
        435                 440                 445 gcc tgg tga                                                             1353
Ala Trp
    450

<210> SEQ ID NO 4
<211> LENGTH: 450
<212> TYPE: PRT
<213> ORGANISM: Homo sapiens

<400> SEQUENCE: 4

Met Asp His Gln Asp Pro Tyr Ser Val Gln Ala Thr Ala Ala Ile Ala
  1               5                  10                  15

Ala Ala Ile Thr Phe Leu Ile Leu Phe Thr Ile Phe Gly Asn Ala Leu
             20                  25                  30

Val Ile Leu Ala Val Leu Thr Ser Arg Ser Leu Arg Ala Pro Gln Asn
         35                  40                  45

Leu Phe Leu Val Ser Leu Ala Ala Ala Asp Ile Leu Val Ala Thr Leu
     50                  55                  60

Ile Ile Pro Phe Ser Leu Ala Asn Glu Leu Leu Gly Tyr Trp Tyr Phe
 65                  70                  75                  80

Arg Arg Thr Trp Cys Glu Val Tyr Leu Ala Leu Asp Val Leu Phe Cys
                 85                  90                  95

Thr Ser Ser Ile Val His Leu Cys Ala Ile Ser Leu Asp Arg Tyr Trp
            100                 105                 110

Ala Val Ser Arg Ala Leu Glu Tyr Asn Ser Lys Arg Thr Pro Arg Arg
        115                 120                 125

Ile Lys Cys Ile Ile Leu Thr Val Trp Leu Ile Ala Ala Val Ile Ser
    130                 135                 140

Leu Pro Pro Leu Ile Tyr Lys Gly Asp Gln Gly Pro Gln Pro Arg Gly
145                 150                 155                 160

Arg Pro Gln Cys Lys Leu Asn Gln Glu Ala Trp Tyr Ile Leu Ala Ser
                165                 170                 175

Ser Ile Gly Ser Phe Phe Ala Pro Cys Leu Ile Met Ile Leu Val Tyr
            180                 185                 190

Leu Arg Ile Tyr Leu Ile Ala Lys Arg Ser Asn Arg Arg Gly Pro Arg
```

```
              195                 200                 205
Ala Lys Gly Gly Pro Gly Gln Gly Glu Ser Lys Gln Pro Arg Pro Asp
    210                 215                 220

His Gly Ala Leu Ala Ser Ala Lys Leu Pro Ala Leu Ala Ser Val
225                 230                 235                 240

Ala Ser Ala Arg Glu Val Asn Gly His Ser Lys Ser Thr Gly Glu Lys
                245                 250                 255

Glu Glu Gly Glu Thr Pro Glu Asp Gly Thr Arg Ala Leu Pro Pro
            260                 265                 270

Ser Trp Ala Ala Leu Pro Asn Ser Gly Gln Gly Gln Lys Glu Gly Val
        275                 280                 285

Cys Gly Ala Ser Pro Glu Asp Glu Ala Glu Glu Glu Glu Glu
    290                 295                 300

Glu Glu Glu Glu Glu Cys Glu Pro Gln Ala Val Pro Val Ser Pro Ala
305                 310                 315                 320

Ser Ala Cys Ser Pro Pro Leu Gln Gln Pro Gln Gly Ser Arg Val Leu
                325                 330                 335

Ala Thr Leu Arg Gly Gln Val Leu Leu Gly Arg Gly Val Gly Ala Ile
            340                 345                 350

Gly Gly Gln Trp Trp Arg Arg Arg Ala Gln Leu Thr Arg Glu Lys Arg
        355                 360                 365

Phe Thr Phe Val Leu Ala Val Val Ile Gly Val Phe Val Leu Cys Trp
370                 375                 380

Phe Pro Phe Phe Phe Ser Tyr Ser Leu Gly Ala Ile Cys Pro Lys His
385                 390                 395                 400

Cys Lys Val Pro His Gly Leu Phe Gln Phe Phe Phe Trp Ile Gly Tyr
                405                 410                 415

Cys Asn Ser Ser Leu Asn Pro Val Ile Tyr Thr Ile Phe Asn Gln Asp
            420                 425                 430

Phe Arg Arg Ala Phe Arg Arg Ile Leu Cys Arg Pro Trp Thr Gln Thr
        435                 440                 445

Ala Trp
    450

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: PCR primer
      pair 1; directed to Homo sapiens

<400> SEQUENCE: 5
ggggcgacgc tcttgtcta                                                    19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: PCR primer
      pair 1; directed to Homo sapiens

<400> SEQUENCE: 6
ggtctccccc tcctccttc                                                    19

<210> SEQ ID NO 7
<211> LENGTH: 18
```

-continued

<212> TYPE: DNA
<213> ORGANISM: Artificial Sequence
<220> FEATURE:
<223> OTHER INFORMATION: Description of Artificial Sequence: PCR primer
      pair 2; directed to Homo sapiens

<400> SEQUENCE: 7
gcagcaaccg cagaggtc                                                       18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: PCR primer
      pair 2; directed to Homo sapiens

<400> SEQUENCE: 8
gggcaagaag cagggtgac                                                      19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: PCR primer
      pair; amplification sense primer; directed to Homo sapiens

<400> SEQUENCE: 9
agggtgtttg tggggcatct                                                     20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: PCR primer
      pair; amplification anti-sense primer; directed to Homo sapiens

<400> SEQUENCE: 10
caagctgagg ccggagacac t                                                   21

METHOD FOR DETECTING A RISK OF HYPERTENSION AND USES THEREOF

FIELD OF THE INVENTION

This invention relates to a method for detecting or diagnosing a risk of, or predisposition to, hypertension in a subject, for targeting antihypertensive treatment in a subject and for selecting subjects for studies testing antihypertensive agents.

BACKGROUND OF THE INVENTION

The publications and other materials used herein to illuminate the background of the invention, and in particular, to provide additional details with respect to the practice, are incorporated by reference.

The $\alpha_2$-adrenoceptors ($\alpha_2$-ARs) mediate many of the physiological effects of the catecholamines norepinephrine and epinephrine. Three genetic subtypes of $\alpha_2$-adrenoceptors are known in humans and other mammals, denoted as $\alpha_{2A}$-, $\alpha_{2B}$- and $\alpha_{2C}$-adrenoceptors. The human genes encoding the receptors are located on chromosomes 10, 2 and 4, respectively. No splice variants are known to exist of these receptors, as the genes are intronless. The tissue distributions and physiological and pharmacological functions of the receptor subtypes have been reviewed e.g. by MacDonald et al. (1997) and Docherty (1998). Based on recent studies with gene-targeted and transgenic mice, $\alpha_{2A}$-adrenoceptors mediate most of the pharmacological actions ascribed to currently available $\alpha_2$-adrenoceptor agonists, including inhibition of neurotransmitter release, central hypotensive and bradycardic effects, sedation and anesthesia, and analgesia. The same studies indicate that $\alpha_{2B}$-adrenoceptors mediate peripheral pressor responses in response to agonist activation (Link et al. 1996, Macmillan et al. 1996) and thus play a significant role in the onset of hypertension (Calzada and Artinano 2001). Other physiological or pharmacological effects have not been associated with certainty with this receptor subtype. The $\alpha_{2C}$-adrenoceptor subtype appears to be involved in regulation of complex behaviors. It is not known that this subtype would have important functions in peripheral tissues outside the central nervous system or in cardiovascular regulation.

Hypertension, like many other common disorders, arises from complex interactions between genetic and environmental factors. It is reasonable to assume that functionally important genetic variation in mechanisms important for the regulation of vascular functions will be found to be associated with the pathogenesis and therapy of hypertension. A variant form of the human $\alpha_{2B}$-AR gene was recently identified (Heinonen et al., 1999). The variant allele encodes a receptor protein with a deletion of three glutamate residues in an acidic stretch of 18 amino acids (of which 15 are glutamates) located in the third intracellular loop of the receptor polypeptide. This acidic stretch is a unique feature in the primary structure of $\alpha_{2B}$-AR in comparison to $\alpha_{2A}$-AR and $\alpha_{2C}$-AR, suggesting that the motif has a distinct role in the function of $\alpha_{2B}$-AR. Amino acid sequence alignment of $\alpha_{2B}$-AR polypeptides of different mammals reveals that the acidic stretch is highly conserved among the $\alpha_{2B}$-A of mammals and that the acidic stretch is long in humans in comparison to other species. This suggests that the motif is important for the functionality of the receptor, and that the short form (D for "deletion") probably represents the ancestral form and the long form (I for "insertion") could well represent a more recent allelic variant in humans. Jewell-Motz and Liggett (1995) studied the in vitro functions of this stretch using site-directed mutagenesis to delete as well as to substitute 16 amino acids of the stretch. Their results suggest that this acidic motif is necessary for full agonist-promoted receptor phosphorylation and desensitisation.

Based on the vasoconstrictive property of $\alpha_{2B}$-AR in mice and the involvement of this acidic region in the desensitisation mechanism of the receptor, we hypothesised that the deletion variant confers reduced receptor desensitisation and therefore augmented vasoconstriction of systemic arteries that could be associated with hypertension. To test this hypothesis, we carried out a population study in 912 middle-aged Finnish men.

SUMMARY OF THE INVENTION

The object of this invention is to provide a method for screening a subject to assess if an individual is at risk to develop hypertension, based on the genotype of $\alpha_{2B}$-adrenoceptor gene and a method to target blood pressure lowering treatments. A further object of the invention is to provide a method for the selection of human subjects for studies testing antihypertensive effects of drugs.

The present invention concerns a method for detecting a risk of hypertension in a subject by determining the pattern of alleles encoding a variant $\alpha_{2B}$-adrenoceptor, i.e. to determine if said subject's genotype of the human $\alpha_{2B}$-adrenoceptor is of the deletion/deletion (D/D) type, comprising the steps of a) providing a biological sample of the subject to be tested, b) providing an assay for detecting in the biological sample the presence of i) the insertion/insertion (I/I) or deletion/insertion (D/I) genotypes of the human $\alpha_{2B}$-adrenoceptor, or ii) the D/D genotype of the human $\alpha_{2B}$-adrenoceptor, the presence of the D/D genotype indicating an increased risk of hypertension in said subject.

According to the invention, the method allows for establishing whether the said subject is of said D/D genotype or not, a presence in the biological sample, such as a blood sample or a buccal sweep, of said D/D genotype thus indicating an increased risk of the subject to develop hypertension, and/or indicating the subject being in need for treatment, such as $\alpha_{2B}$-selective or $\alpha_{2B}$-nonselective $\alpha_2$-adrenoceptor antagonist therapy.

The said method can thus include a step of identifying a subject having an increased risk to develop hypertension, and/or a subject in need of therapy, such as $\alpha_{2B}$-selective or $\alpha_{2B}$-nonselective $\alpha_2$-adrenoceptor antagonist therapy for hypertension.

The invention also concerns a method as defined comprising the further steps of c) assessing at least one of the two following i) the subject's risk to develop hypertension, or ii) the subject's need for $\alpha_{2B}$-selective or $\alpha_{2B}$-nonselective $\alpha_2$-adrenoceptor antagonist therapy for hypertension, based on whether said subject is of said D/D genotype or not.

A further object of the invention is a method for treating, or targeting the treatment of hypertension in a hypertensive subject by determining the pattern of alleles encoding a variant $\alpha_{2B}$-adrenoceptor, i.e. by determining if said subject's genotype of the human $\alpha_{2B}$-adrenoceptor is of the deletion/deletion (D/D) type, comprising the steps presented above, and treating a subject of the D/D genotype with a drug affecting the noradrenaline sensitivity or sympathetic activity of the subject.

The present invention is also directed to a kit for detecting a risk of hypertension in a subject, or for selecting a subject for targeting antihypertensive treatment or studies for testing antihypertensive agents, comprising means for determining the pattern of alleles encoding a variant $\alpha_{2B}$-adrenoceptor in a biological sample, as well as its use.

The invention also provides a DNA sequence comprising a nucleotide sequence encoding a variant $\alpha_{2B}$-adrenoceptor protein with a deletion of at least 1 glutamate from a glutamic acid repeat element of 12 glutamates, amino acids 298–309, in an acidic stretch of 18 amino acids 294–311, located in the $3^{rd}$ intracellular loop of the receptor polypeptide.

The invention further provides a variant $\alpha_{2B}$-adrenoceptor protein with a deletion of at least 1 glutamate from a glutamic acid repeat element of 12 glutamates, amino acids 298–309, in an acidic stretch of 18 amino acids 294–311, located in the $3^{rd}$ intracellular loop of the receptor polypeptide.

DETAILED DESCRIPTION OF THE INVENTION

The present invention relates to a DNA molecule encoding a variant human $\alpha_{2B}$-adrenoceptor, said variant $\alpha_{2B}$-adrenoceptor protein and a method to assess the risk of individuals to develop hypertension in mammals as well as a method for the targeting treatment for hypertension.

The word treating shall also be understood to include preventing.

The concept "a deletion of at least 1 glutamate from a glutamic acid repeat element of 12 glutamates" refers to any deletion of 1 to 12 glutamates irrespective of the specific location in, or how many glutamates from said repeat element of 12 glutamates, amino acids 298–309 (SEQ ID NO: 4), in an acidic stretch of 18 amino acids 294–311 located in the $3^{rd}$ intracellular loop of the receptor polypeptide are deleted.

The concept "deletion/deletion (D/D) genotype of the human $\alpha_{2B}$-adrenoceptor", in short "D/D genotype", refers to a genotype of an individual having both ($\alpha_{2B}$-adrenoceptor alleles code for a variant $\alpha_{2B}$-adrenoceptor with a deletion of at least 1 glutamate from a glutamic acid repeat element of 12 glutamates, amino acids 298–309, in an acidic stretch of 18 amino acids 294–311 (SEQ ID NO: 4), located in the $3^{rd}$ intracellular loop of the receptor polypeptide. Correspondingly "deletion/insertion (D/I) genotype" refers to a genotype having one of the gene alleles code for an ($\alpha_{2B}$-adrenoceptor with a said deletion and the other without a said deletion, i.e. with a respective insertion, and thus the "insertion/insertion (I/I) genotype" refers to a genotype having both alleles code for an $\alpha_{2B}$-adrenoceptor without said deletion or deletions.

A common variant form (SEQ ID NO: 1) of the human $\alpha_{2B}$-AR gene (SEQ ID NO: 3) was recently identified (Heinonen et al. 1999). This variant gene encodes a receptor protein (SEQ ID NO: 2) with a deletion of 3 glutamates, amino acids 307–309, from a glutamic acid (Glu) repeat element of 12 glutamates, amino acids 298–309, in an acidic stretch of 18 amino acids 294–311 (SEQ ID NO: 4), located in the $3^{rd}$ intracellular loop of the receptor polypeptide. This variant gene (SEQ ID NO: 1) was associated with decreased basal metabolic rate (BMR) in a group of obese Finnish subjects (Heinonen et al. 1999). Of the 166 obese subjects, 47 (28%) were homozygous for the long 12 glutamate repeat element ($Glu^{12}/Glu^{12}$), whereas 90 (54%) were heterozygous ($Glu^{12}/Glu^9$) and 29 (17%) were homozygous for the short form ($Glu^9/Glu^9$).

The results to be presented below show that in a population sample of 912 Finnish middle-aged men subjects homozygous for the short form ($Glu^9/Glu^9$) described above, thus representing a deletion/deletion (D/D) genotype of the $\alpha_{2B}$-adrenoceptor, have a significantly elevated risk for hypertension. Based on these results and previous publications referred to above it can be postulated that this D/D genotype is related to an impaired capacity to downregulate $\alpha_{2B}$-adrenoceptor function during sustained receptor activation. Since altered $\alpha_{2B}$-adrenoceptor function seems to be of relevance in the pathogenesis of hypertension, we believe it could also be of relevance in subjects with the insertion/deletion (I/D) (heterozygous $Glu^{12}/Glu^9$) and insertion/insertion (I/I) (homozygous $Glu^{12}/Glu^{12}$) genotypes when other risk factors for hypertension are present. Further, since this specific deletion of 3 glutamates from said glutamic acid repeat element of 12 glutamates, amino acids 298–309, in said acidic stretch of 18 amino acids 294–311, located in the $3^{rd}$ intracellular loop of the receptor polypeptide seems to be of relevance in hypertension we believe that also other deletions, i.e. deletions of at least 1 glutamate, from said glutamic acid repeat element of 12 glutamates, amino acids 298–309, could be of relevance in the pathogenesis of hypertension, because the $3^{rd}$ intracellular loop of the receptor polypeptide it is located in seems to have an essential role in the down-regulation of the $\alpha_{2B}$-adrenoceptor. Thus persons with the D/D genotype have chronically up-regulated $\alpha_{2B}$-adrenoceptors, leading to the elevation of systemic blood pressure.

$\alpha_{2B}$-adrenoceptors mediate contraction of arteries, and genetic polymorphism present in the $\alpha_{2B}$-adrenoceptor gene renders some subjects more susceptible to $\alpha_{2B}$-adrenoceptor mediated vasoconstriction of the blood pressure regulating resistance arteries (arteriolies) and associated clinical disorders such as hypertension. These subjects will especially benefit from treatment with an $\alpha_{2B}$-adrenoceptor antagonist, and will be at increased risk for adverse effects if subtype-nonselective $\alpha_2$-agonists are administered to them. Therefore, a gene test recognizing subjects with a deletion variant of the $\alpha_{2B}$-adrenoceptor gene will be useful in diagnostics and patient selection for specific therapeutic procedures and clinical drug testing trials. A gene test recognizing the D/D genotype of the $\alpha_{2B}$-adrenoceptor is useful in assessing an individual's risk to develop hypertension related to the D/D genotype. The test can be used to set a specific subdiagnosis of hypertension, based on its genetic etiology.

Furthermore, a gene test recognizing the D/D genotype of the $\alpha_{2B}$-adrenoceptor is useful in selecting drug therapy for patients with hypertension. Such drugs are e.g. a drug modulating, inhibiting or activating the vascular alpha- or beta-adrenargic receptors of the subjects either directly or through central nervous system effects, for example pindolol, propranolol, sotalol, timolol, acebutolol, atenol, betaxolol, bisoprol, esmolol, metoprolol, seliprol, carvedilol, labetalol, clonidine, moxonidine, prazosin, or indapamid, including α-adrenoceptor antagonists ($\alpha_{2B}$-selective or nonselective).

For instance, as angiotensin II causes an increase of noradrenaline sensitivity, and this effect is at least in part mediated by α-adrenoceptors (Datte et al. 2000), the blood pressure lowering effect of drugs acting through angiotensin II inhibition, such as the angiotensin (AT) receptor blockers, is conceivably enhanced in persons with the D/D genotype of the $\alpha_{2B}$-adrenoceptor. Such drugs are for example captopril, cinapril, enalapril, imidapril, lisinopril, moexipril, perindopril, ramipril, trandolapril, candesartan, eprosartan, irbesartan, losartan, valsartan or telmisartan.

A gene test recognizing the D/D genotype of the $\alpha_{2B}$-adrenoceptor is useful in selecting drug therapy for patients who might be at increased risk for adverse effects of $\alpha_2$-adrenergic agonists; either it will be possible to avoid the use of $\alpha_2$-agonists in such patients, or it will be possible to include a specific $\alpha_{2B}$-antagonist in their therapeutic regimen.

On the other hand, it is conceivable that the patients with other than the D/D genotype will benefit more from other antihypertensive drugs.

The DNA sequence can be used for screening a subject to determine if said subject is a carrier of a variant gene. The determination can be carried out either as a DNA analysis according to well known methods, which include direct DNA sequencing of the normal and variant gene, allele specific amplification using the polymerase chain reaction (PCR) enabling detection of either normal or variant sequence, or by indirect detection of the normal or variant gene by various molecular biology methods including e.g. PCR-single stranded conformation polymorphism (SSCP) method or denaturing gradient gel electrophoresis (DGGE). Determination of the normal or variant gene can also be done by using a restriction fragment length polymorphism (RFLP) method, which is particularly suitable for genotyping large numbers of samples. Similarly, a test based on gene chip or array technology can be easily developed in analogy with many currently existing such tests for single-nucleotide polymorphisms.

The determination can also be carried out at the level of RNA by analyzing RNA expressed at tissue level using various methods. Allele specific probes can be designed for hybridization. Hybridization can be done e.g. using Northern blot, RNase protection assay or in situ hybridization methods. RNA derived from the normal or variant gene can also be analyzed by converting tissue RNA first to cDNA and thereafter amplifying cDNA by an allele specific PCR method.

The kit for use in the method according to the invention preferably contains the various components needed for carrying out the method packaged in separate containers and/or vials and including instructions for carrying out the method. Thus, for example, some or all of the various reagents and other ingredients needed for carrying out the determination, such as buffers, primers, enzymes, control samples or standards etc can be packaged separately but provided for use in the same box. Instructions for carrying out the method can be included inside the box, as a separate insert, or as a label on the box and/or on the separate vials. The kit may also contain the necessary software needed to interpret the results obtained with the kit, or for utilizing the results from a gene chip used in the method.

The invention will be described in more detail in the experimental section.

EXPERIMENTAL SECTION

Determination of Genomic Alleles Encoding the $\alpha_{2B}$-Adrenoceptor

PCR-SSCA Analysis

The polymerase chain reaction-single stranded conformational analysis (PCR-SSCA) used to identify the genomic alleles encoding the $\alpha_{2B}$-adrenoceptor was carried out as follows: The genomic DNA encoding the $\alpha_{2B}$-adrenergic receptor was amplified in two parts specific for the intronless $\alpha_{2B}$-adrenoceptor gene sequence (Lomasney et al. 1990). The PCR primer pairs for PCR amplification were as follows: Pair 1:5'-GGGGCGACGCTCTTGTCTA-3' (SEQ ID NO: 5) and 5'-GGTCTCCCCCTCCTCCTTC-3' (SEQ ID NO: 6) (product size 878 bp), pair 2:5'-GCAGCAACCG-CAGAGGTC-3' (SEQ ID NO: 7) and 5'-GGGCAAGAAG-CAGGGTGAC-3' (SEQ ID NO: 8) (product size 814 bp). The primers were delivered by KeboLab (Helsinki, Finland). PCR amplification was conducted in a 5 µl volume containing 100 ng genomic DNA (isolated from whole blood), 2.5 mmol/l of each primer, 1.0 mmol/l deoxy-NTPs, 30 nmol/l $^{33}$P-dCTP and 0.25 U AmpliTaq DNA polymerase (Perkin Elmer Cetus, Norwalk, Conn.). PCR conditions were optimized using the PCR Optimizer™ kit (Invitrogen, San Diego, Calif.). Samples were amplified with a GeneAmp PCR System 9600 (Perkin Elmer Cetus). PCR products were digested with restriction enzymes for SSCA analysis. The product of primer pair 1 was digested with Dde I and Dra III (Promega Corp., Madison, Wis.). The product of primer pair 2 was digested with Alu I and Hinc II (Promega Corp.). The digested samples were mixed with SSCA buffer containing 95% formamide, 10 mmol/l NaOH, 0.05% xylene cyanol and 0.05% bromophenol blue (total volume 25 µl). Before loading, the samples were denatured for 5 min at 95° C. and kept 5 min on ice. Three microliters of each sample were loaded on MDE™ high-resolution gel (FMC, BioProducts, Rockland, Mass.). The gel electrophoresis was performed twice, at two different running conditions: 6% MDE gel at +4° C. and 3% MDE gel at room temperature, both at 4 W constant power for 16 h. The gels were dried and autoradiography was performed by apposing to Kodak BioMax MR film for 24 h at room temperature.

Sequencing and Genotyping

DNA samples migrating at different rates in SSCA were sequenced with the Thermo Sequenase™ Cycle Sequencing Kit (Amersham Life Science, Cleveland, Ohio).

For genotyping the identified 3-glutamic acid deletion, DNA was extracted from peripheral blood using standard methods. The $\alpha_{2B}$-AR I/D genotype was determined by separating PCR-amplified DNA fragments with electrophoresis. Based on the nature of the I/D variant, identification of the long and short alleles was achieved by their different electrophoretic migration rates due to their 9 bp size difference.

The region of interest was amplified using a sense primer 5'-AGG-GTG-TTT-GTG-GGG-CAT-CT-3' (SEQ ID NO:9) and an anti-sense primer 5'-CAA-GCT-GAG-GCC-GGA-GAC-ACT-3' (SEQ ID NO: 10)(Oligold, Eurogentec, Belgium), yielding a product size of 112 bp for the long allele (I) and 103 bp for the short allele (D). PCR amplification was conducted in a 10 µL volume containing ~100 ng genomic DNA, 1× buffer G (Invitrogen, San Diego, Calif., USA), 0.8 mM dNTPs, 0.3 µM of each primer and 0.25 units of AmpliTaq DNA polymerase (Perkin Elmer Cetus, Norwalk, Conn., USA). Samples were amplified with a Gene-Amp PCR System 9600 (Perkin Elmer Cetus). After initial denaturation at 94° C. for 2 minutes, the samples were amplified over 35 cycles. PCR amplification conditions were 96° C. (40 s), 69° C. (30 s) and 72° C. (30 s) followed by final extension at 72° C. for 6 minutes. The PCR products representing the long and short alleles were identified by two alternative methods. 1) The amplified samples were mixed with 4 µl of stop solution (Thermo Sequenase™ Cycle Sequencing kit), heated to 95° C. for 2 min, and loaded hot onto sequencing gels (Long Ranger™, FMC). The gels were dried and autoradiography was performed as previously described. 2) Separation of the amplified PCR products was performed with electrophoresis on a high-resolution 4% Metaphor agarose gel (FMC Bioproducts, Rockland, Me.) and the bands were visualized by ethidium bromide staining. In both methods, the long ($Glu^{12}$) and short ($Glu^9$) alleles were identified based on their different electrophoretic migration rates.

Population Study

The above referred population study of 912 Finnish middle-aged men subjects including 192 subjects with a specific deletion/deletion (D/D) genotype of the $\alpha_{2B}$-adrenoceptor is described in more detail in the following:

Knowing the vasoconstrictive property of $\alpha_{2B}$-AR in mice and the possible involvement of the investigated acidic region in the desensitization mechanism of the receptor we hypothesized that the observed insertion/deletion allelic variation could be associated with hypertension. To test this hypothesis, we carried out a population study in 912 middle-aged Finnish men with no prior history of coronary heart disease. The study was carried out as part of the Kuopio Ischemic Heart Disease Risk Factor Study (KIHD), which is an ongoing population-based study designed to investigate risk factors for cardiovascular diseases and related outcomes in men from eastern Finland (Salonen 1988). This area is known for its homogenous population (Sajantila et al. 1996) and high coronary morbidity and mortality rates (Keys 1980).

Of the 912 subjects, 192 (21%) had the D/D genotype, 256 (28%) had the I/I genotype and 464 (51%) were heterozygous i.e. I/D. This genotype distribution is in Hardy-Weinberg equilibrium (p=0.46).

Four hundred and seventeen men had no family history of hypertension, and 495 had hypertension in the family (either parents or siblings or both). It was assumed that genetic traits would have a stronger association with hypertension in the subjects who had a history of hypertension in the family, and thus the association between the $\alpha_{2B}$-adrenoceptor genotype and hypertension was analyzed separately in men with and without family history (Tables 1 and 2). In a multivariate linear regression model, men with the DD genotype had on the average a higher mean systolic blood pressure (BP) as compared with the other genotypes (p=0.021) among men with a family history (Table 1). Among those with a family history of hypertension, DD homozygous men had, in a multivariate logistic model, a 2.04-fold (95% confidence interval 1.06 to 3.93, p=0.032) probability (prevalence) of hypertension (either systolic BP at least 165 mmHg or diastolic BP at least 95 mmHg or antihypertensive medication, Table 2).

The association of the use of α-adrenoceptor antagonists such as prazosin with hypertension was analyzed among the DD homozygous men and other men, separately. The antihypertensive effect was estimated as the blood pressure difference between the specific drug type vs other drugs. In men with the DD genotype but not among the other men, the use of a-adrenoceptor antagonists was associated with a lowering of both systolic and diastolic blood pressure as well as decreased occurrence of a number of self-reported adverse effects. Among 440 men who were hypertensive at the 11-year follow-up (systolic BP≧165 mmHg or diastolic BP≧95 mmHg or antihypertensive treatment), among men with the D/D $\alpha_{2B}$-adrenoceptor genotype, the means systolic BP was 111 mmHg in those treated with alpha-blocker and 137 mmHg in those treated with other drugs, whereas these means were 150 mmHg and 138 mmHg in men with other genotypes. There was a similar trend for beta-adrenoceptor antagonists (beta-blockers) such as atenolol, metoprolol and pindolol, as well as for angiotensin converting enzyme (ACE) inhibitors such as captopril, enalapril and lisinopril. For example, among 344 men, who were hypertensive in the KIED baseline examination the mean systolic blood pressure was 11 years later among subjects with D/D genotype 134 mmHg in those treated with beta-blocker and 141 mmHg among those treated with other drugs, whereas for men with other genotypes these means were 137 and 138 mmHg. Among the 440 men who were hypertensive at the 11-year follow-up, in those with the D/D genotype, the mean systolic BP was 133 in beta-blocker treated and 139 in others, whereas in men with other genotypes these means were 139 and 138 mmHg. Among men who were treated with β-blockers, the mean systolic blood pressure was 128.8 (SD 16.2) in those with the D/D genotype and 135.5 mmHg (SD 19.3) in those with other genotypes (p=0.04 for difference). In a linear covariance model adjusting for age and body-mass index (kg/m2), the genotype-β-blocker interaction was statistically significant (1-sided p=0.04).

The antihypertensive effect of antihypertensive drug types acting through other mechanisms than adrenoceptor or noradrenaline sensitivity modulation and was greater in men with other than the D/D genotype. For example, the blood pressure lowering effect of diuretics and calcium channel blockers was larger in $\alpha_{2B}$-AR genotypes other than D/D. Men with the DD genotype had an increased prevalence of adverse effects and a smaller antihypertensive response during $\alpha_2$-adrenoceptor agonist therapy such as clonidin.

Taken together, the known biological properties of the $\alpha_{2B}$-AR, the homogeneity of the Finnish population, the study design, the relatively large representative study population and the association of hypertension with one trait suggest that the D/D receptor allele is a causal genetic risk factor for hypertension.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

TABLE 1

The strongest risk factors for the mean systolic blood presure in linear regresssion models among men with no family history of hypertension and in those with a family history.

| | No family history of hypertension | | | Family history of hypertension | | |
|---|---|---|---|---|---|---|
| Risk factor | Coefficient | 95% CI | P | Coefficient | 95% CI | P |
| $\alpha_{2B}$-AR genotype (DD vs. other) | −0.44 | −3.83, 2.95 | 0.799 | 3.87 | 0.59, 7.16 | 0.021 |
| Body-mass index (kg/m2) | 1.06 | 0.67, 1.46 | <0.001 | 0.84 | 0.44, 1.24 | <0.001 |

TABLE 1-continued

The strongest risk factors for the mean systolic blood presure in linear regresssion models among men with no family history of hypertension and in those with a family history.

| Risk factor | No family history of hypertension | | | Family history of hypertension | | |
|---|---|---|---|---|---|---|
| | Coefficient | 95% CI | P | Coefficient | 95% CI | P |
| Age (years) | 0.62 | 0.40, 0.85 | <0.001 | 0.77 | 0.57, 0.98 | <0.001 |
| Resting heart rate (bpm) | 0.19 | 0.05, 0.32 | 0.006 | 0.36 | 0.22, 0.49 | <0.001 |
| Fasting blood glucose (umol/L) | 0.85 | −0.37, 2.07 | 0.172 | 2.23 | 0.89, 3.56 | 0.001 |
| Alcohol from beer (g/wk) | 0.002 | −0.002, 0.03 | 0.092 | 0.04 | 0.02, 0.06 | 0.001 |
| Use of beta-blocking agent (yes vs. no) | −3.0 | −9.0, 3.0 | 0.327 | 6.9 | 2.5, 11.2 | 0.002 |
| Family history of cancer | −1.6 | −4.8, 1.5 | 0.306 | 2.0 | −1.1, 5.1 | 0.200 |
| R square for the model | 0.170 | | | 0.261 | | |

TABLE 2

Probability of systolic hypertension and its 95% confidence interval, related with α$_{2B}$-AR genotype and other strongest risk factors in men free of family history of hypertension and in those with a family history. Results are from logistic regression models.

| Risk factor | No family history of hypertension | | | Family history of hypertension | | |
|---|---|---|---|---|---|---|
| | Relative risk | 95% CI | P | Relative risk | 95% CI | P |
| α$_{2B}$-AR genotype (DD vs. other) | 0.61 | 0.22, 1.67 | 0.333 | 2.04 | 1.06, 3.93 | 0.032 |
| Body-mass index (kg/m2) | 1.23 | 1.12, 1.36 | <0.001 | 1.11 | 1.02, 1.21 | 0.015 |
| Age (years) | 1.12 | 1.04, 1.20 | 0.001 | 1.10 | 1.05, 1.15 | <0.001 |
| Resting heart rate (bpm) | 0.98 | 0.95, 1.02 | 0.384 | 1.03 | 1.003, 1.06 | 0.032 |
| Fasting blood glucose (umol/L) | 1.25 | 0.97, 1.60 | 0.085 | 1.28 | 1.03, 1.60 | 0.027 |
| Alcohol from beer (g/wk) | 1.00 | 1.00, 1.01 | 0.083 | 1.004 | 1.00, 1.01 | 0.036 |
| Use of beta-blocking agent (yes vs. no) | 0.001 | 0.00, 521 | 0.725 | 3.09 | 1.42, 6.70 | 0.004 |
| Family history of cancer | 0.57 | 0.23, 1.45 | 0.242 | 2.02 | 1.07, 3.82 | 0.031 |
| Number of hypertensives | 31 | | | 60 | | |
| Number of men | 417 | | | 495 | | |
| R square for the model | 0.202 | | | 0.219 | | |

REFERENCES

Calzada B C, Artinano A L. Alpha-adrenoceptor subtypes. *Phanmacol Res* 2001;44:195–208.

Datte J- Y, Gohlke P, Pees C, Ziegler A. Short treatments of normotensive and hypertensive rats by angiotensin II and nitric oxide inhibitor induce and increase of noradrenaline sensitivity in isolated vena portae preparations. *Pharmacol Res* 2000;41 :641–648.

Docherty J R: Subtypes of functional α$_1$- and α$_2$-receptors. *Eur J Pharmacol* 1998;361:1–15

Heinonen P, Koulu M, Pesonen U, Karvonen M, Rissanen A, Laakso M, Valve R, Uusitupa M, Scheinin M: Identification of a three amino acid deletion in the alpha-2B-adrenergic receptor which is associated with reduced basal metabolic rate in obese subjects. *J Clin Endocrinol Metab* 1999;84:2429–2433

Jewell-Motz E, Liggett S B: An acidic motif within the third intracellular loop of the alpha2C2 adrenergic receptor is required for agonist- promoted phosphorylation and desensitization. *Biochemistry* 1995;34:11946–11953

Keys A: *Seven Countries: A Multivariate Analysis of Death and Coronary Heart Disease*. Cambridge, Mass., Harvard University Press, 1980

Link R E, Desai K, Hein L, Stevens M E, Chruscinski A, Bernstein D, Barsh G S, Kobilka B K: Cardiovascular regulation in mice lacking alph2-adrenergic receptor subtypes b and c. *Science* 1996;273:803–805.

Lomasney J W, Lorenz W, Allen L F, King K, Regan J W, Yang-Feng T L, Caron M C, Lefkowitz R J: Expansion of the alpha-2 adrenergic receptor family: cloning and characterization of a human alpha-2 adrenergic receptor subtype, the gene for which is located on chromosome 2. *Proc Natl Acad Sci USA*. 1990;87:5094–5098.

MacDonald E, Kobilka B K, Scheinin M: Gene targeting—homing in on α$_2$-adrenoceptor subtype function. *Trends Pharmacol Sci* 1997; 18:211–219

MacMillan L B, Hein L, Smith M S, Piascik M T, Limbird L E: Central hypotensive effects of the alph2a-adrenergic receptor subtype. *Science* 1996;273:801–803

Sajantila A, Salem A H, Savolainen P, Bauer K, Gierig C, Paabo S: Paternal and maternal DNA lineages reveal a bottleneck in the founding of the Finnish population. *Proc.Natl.Acad.Sci.U.S.A.* 1996;93:12035–12039

Salonen J T: Is there a continuing need for longitudinal epidemiologic research? The Kuopio Ischaemic Heart Disease Risk Factor Study. *Ann.Clin Res* 1988;20:46–50

The invention claimed is:

1. A method for detecting a risk of hypertension in a subject having a family a history of hypertension by determining the pattern of alleles encoding a variant $\alpha_{2B}$-adrenoceptor, comprising the steps of:
   a) providing a biological sample of the subject to be tested; and
   b) performing an assay on the biological sample for dectecting in the biological sample the presence of
      i) the insertion/insertion (I/I) or deletion/insertion (D/I) genotypes of the human $\alpha_{2B}$-adrenoceptor, or
      ii) the D/D genotype of the human $\alpha_{2B}$-adrenoceptor, wherein the presence of the D/D genotype indicates an increased risk of hypertension in said subject.

2. The method according to claim 1, wherein the assay is a DNA-assay.

3. The method according to claim 1 or 2, wherein the assay is carried out using a gene or DNA chip, microarray, strip, panel or similar combination of more than one genes, mutations or RNA expressions to be assayed.

4. The method according to claim 1, wherein the allelic pattern is determined using polymerase chain reaction.

5. The method according to claim 1, wherein the biological sample is a blood sample or buccal sweep sample and genomic DNA is isolated from the said sample.

6. The method according to claim 1, wherein the assay is based on a capturing probe which comprises a single strand of the cDNA, comprising a nucleotide sequence encoding a variant $\alpha_{2B}$-adrenoceptor protein with a deletion of at least 1 glutamate from a glutamic acid repeat element of 12 glutamates, amino acids 298–309, in an acidic stretch of 18 amino acids 294–311, located in the $3^{rd}$ intracellular loop of the receptor polypeptide.

7. The method according to claim 1, wherein the assay is based on a capturing probe which comprises a single strand of the cDNA corresponding to the $\alpha_{2B}$-adrenoceptor without the deletion of a glutamate from a glutamic acid repeat element of 12 glutamates, amino acids 298–309, in an acidic stretch of 18 amino acids 294–311, located in the $3^{rd}$ intracellular loop of the receptor polypeptide.

8. The method according to claim 1, wherein the method is used for determining whether a subject will benefit from treatment with a drug affecting the noradrenaline sensitivity or sympathetic activity of the subject.

9. The method according to claim 1, wherein the method is used for determining whether a subject will benefit from treatment with an $\alpha_{2B}$-adrenoceptor antagonist.

10. The method according to claim 1, wherein the method is used for determining whether a subject will be at increased risk of adverse effects if subtype-nonselective $\alpha_2$-agonists or a diuretic or a calcium channel blocker are administered to them.

11. The method according to claim 1, further comprising the step of selecting a subject of the D/D genotype for clinical drug trials testing the antihypertensive effects of compounds.

12. The method according to claim 11, wherein the compound is a drug affecting the noradrenaline sensitivity or sympathetic activity of the subject.

13. The method according to claim 8 or 11, wherein the compound is a drug modulating, inhibiting or activating the vascular alpha- or beta-adrenergic receptors of the subjects either directly or through central nervous system effects.

14. The method according to claim 8 or 11, wherein the compound is an angiotensin converting enzyme (ACE) inhibitor, angiotensin II inhibitor or angiotensin receptor inhibitor.

15. The method according to claim 13, wherein the compound is an $\alpha_{2B}$-selective or $\alpha_{2B}$-nonselective $\alpha_2$-adrenoceptor antagonist.

16. A method for targeting the treatment of hypertension in a hypertensive subject having a family history of hypertension by determining the pattern of alleles encoding a said variant $\alpha_{2B}$-adrenoceptor in accordance with the method of, claim 1, and treating a subject having the D/D genotype with a drug affecting the noradrenaline sensitivity or sympathetic activity of the subject.

17. The method according to claim 16, wherein the said drug is a drug modulating, inhibiting or activating the vascular alpha- or beta-adrenergic receptors of the subjects either directly or through central nervous system effects.

18. The method according to claim 17, wherein the said drug is pindolol, propranolol, sotalol, timolol, acebutolol, atenol, betaxolol, bisoprol, esmolol, metoprolol, seliprol, carvedilol, labetalol, clonidine, moxonidine, prazosin, or indapamid.

19. The method according to claim 16, wherein the said drug is an angiotensin converting enzyme (ACE) inhibitor, angiotensin II inhibitors or angiotensin receptor inhibitor.

20. The method according to claim 19, wherein the said drug is captopril, cinapril, enalapril, imidapril, lisinopril, moexipril, perindopril, ramipril, trandolapril, candesartan, eprosartan, irbesartan, losartan, valsartan or telmisartan.

21. A method according to claim 17, wherein the said drug is an $\alpha_{2B}$-selective or $\alpha_{2B}$-nonselective $\alpha_2$-adrenoceptor or $\alpha$-adrenoceptor antagonist.

* * * * *